United States Patent
Doubet (10) Patent No.: US 11,337,894 B2
(45) Date of Patent: May 24, 2022

(54) SYRINGE ADAPTER FOR ANIMAL MEDICATION

(71) Applicant: James T. Doubet, Parker, CO (US)

(72) Inventor: James T. Doubet, Parker, CO (US)

( * ) Notice: Subject to any disclaimer, the term of this patent is extended or adjusted under 35 U.S.C. 154(b) by 1014 days.

(21) Appl. No.: 16/010,155

(22) Filed: Jun. 15, 2018

(65) Prior Publication Data
US 2019/0380911 A1 Dec. 19, 2019

(51) Int. Cl.
*A61J 1/20* (2006.01)
*A61D 7/00* (2006.01)

(52) U.S. Cl.
CPC .............. *A61J 1/2096* (2013.01); *A61D 7/00* (2013.01); *A61J 1/2048* (2015.05)

(58) Field of Classification Search
CPC ........ A61M 2039/1077; A61M 5/1782; A61M 25/0068; A61M 2205/195; A61J 1/2048; A61J 1/2096; A61D 7/00
See application file for complete search history.

(56) References Cited

U.S. PATENT DOCUMENTS

| | | | |
|---|---|---|---|
| 822,079 A | 5/1906 | Roussy | |
| 2,626,603 A | 1/1953 | Gabriel | |
| 2,752,919 A | 7/1956 | Gabriel | |
| 3,320,954 A | 5/1967 | Cowley | |
| 3,436,828 A | 4/1969 | Dragan | |
| 3,958,570 A | 5/1976 | Vogelman et al. | |
| 4,046,145 A | 9/1977 | Choksi et al. | |
| 4,294,250 A | 10/1981 | Dennehey | |
| 4,316,462 A | 2/1982 | Baker | |
| 4,338,925 A | 7/1982 | Miller | |
| 4,472,141 A | 9/1984 | Dragan | |
| 4,664,655 A | 5/1987 | Orentreich et al. | |
| 4,758,158 A | 7/1988 | Pierce et al. | |
| 4,758,234 A | 7/1988 | Orentreich et al. | |
| 4,927,417 A | 5/1990 | Moncada et al. | |

(Continued)

FOREIGN PATENT DOCUMENTS

| | | |
|---|---|---|
| EP | 1923086 B1 | 4/2012 |
| KR | 20120107161 A | 10/2012 |

(Continued)

OTHER PUBLICATIONS

"(Revised) List of Patents and/or Patent Applications to be Treated as Related". Dec. 18, 2020. 2 pages.

(Continued)

*Primary Examiner* — Bhisma Mehta
*Assistant Examiner* — Rachel T. Smith
(74) *Attorney, Agent, or Firm* — Marcia L. Doubet (57) ABSTRACT

Improved apparatus for use with animal medication in fluid form, which is particularly beneficial for medications having a relatively high viscosity. The disclosed syringe adapter has an opening that is relatively large, as compared to a conventional needle, and thus affixing the disclosed syringe adapter to a syringe improves syringeability of higher-viscosity medications. When the disclosed syringe adapter is affixed to a pistol-grip or tab-handled syringe, the medication withdrawn into the pistol-grip syringe can be more easily administered from the syringe barrel (noting that the syringe adapter will be replaced with a needle prior to injecting the medication).

20 Claims, 5 Drawing Sheets

(56) References Cited

U.S. PATENT DOCUMENTS

| | | | |
|---|---|---|---|
| 5,047,021 | A | 9/1991 | Utterberg |
| 5,195,985 | A | 3/1993 | Hall |
| 5,322,510 | A | 6/1994 | Lindner et al. |
| 5,445,523 | A | 8/1995 | Fischer et al. |
| 5,509,911 | A | 4/1996 | Cottone et al. |
| 5,733,258 | A | 3/1998 | Lane |
| 5,746,733 | A | 5/1998 | Capaccio et al. |
| 6,117,113 | A | 9/2000 | Novacek et al. |
| 6,511,472 | B1 | 1/2003 | Hayman et al. |
| 6,787,568 | B1 | 9/2004 | Mihalik |
| 6,790,867 | B2 | 9/2004 | Kohan et al. |
| 6,981,618 | B2 | 1/2006 | Reisinger |
| 7,347,458 | B2 | 3/2008 | Rome et al. |
| 7,472,932 | B2 | 1/2009 | Weber et al. |
| 7,682,343 | B2 | 3/2010 | Westbye |
| 7,699,609 | B2 | 4/2010 | Lawter et al. |
| 7,803,139 | B2 | 9/2010 | Fangrove, Jr. |
| 8,034,845 | B2 | 10/2011 | Freehauf et al. |
| 8,044,102 | B2 | 10/2011 | Kohan et al. |
| D736,915 | S | 8/2015 | Schultz |
| 9,295,788 | B2 | 3/2016 | Green |
| 9,801,788 | B2 | 10/2017 | Banik et al. |
| 10,709,850 | B2 | 7/2020 | Doubet et al. |
| 11,071,834 | B2 | 7/2021 | Doubet et al. |
| 11,090,444 | B2 | 8/2021 | Doubet et al. |
| 11,097,058 | B2 | 8/2021 | Doubet et al. |
| 11,173,257 | B2 | 11/2021 | Doubet |
| 2002/0173753 | A1 | 11/2002 | Caizza et al. |
| 2003/0236501 | A1 | 12/2003 | Donnan et al. |
| 2004/0039365 | A1 | 2/2004 | Aramata et al. |
| 2004/0068266 | A1 | 4/2004 | Delmotte |
| 2004/0116873 | A1 | 6/2004 | Fojtik |
| 2006/0047251 | A1 | 3/2006 | Bickford Smith et al. |
| 2006/0270996 | A1 | 11/2006 | Fojtik |
| 2006/0271015 | A1 | 11/2006 | Mantell |
| 2007/0060898 | A1 | 3/2007 | Shaughnessy et al. |
| 2007/0183986 | A1 | 8/2007 | Allred et al. |
| 2007/0203451 | A1 | 8/2007 | Murakami et al. |
| 2008/0015539 | A1 | 1/2008 | Pieroni et al. |
| 2008/0188816 | A1 | 8/2008 | Shimazaki et al. |
| 2008/0287884 | A1 | 11/2008 | Warden et al. |
| 2009/0182284 | A1 | 7/2009 | Morgan |
| 2009/0227894 | A1 | 9/2009 | Fojtik |
| 2011/0028909 | A1 | 2/2011 | Lum et al. |
| 2012/0184938 | A1 | 7/2012 | Lev et al. |
| 2013/0018354 | A1 | 1/2013 | Sund et al. |
| 2013/0178806 | A1 | 7/2013 | Felix-Faure et al. |
| 2013/0331810 | A1 | 12/2013 | Bazala et al. |
| 2014/0066840 | A1 | 3/2014 | Mantell |
| 2014/0261860 | A1 | 9/2014 | Heath et al. |
| 2017/0165192 | A1 | 6/2017 | Georges et al. |
| 2017/0203086 | A1 | 7/2017 | Davis |
| 2018/0050183 | A1 | 2/2018 | Taylor |
| 2018/0344570 | A1 | 12/2018 | Davis et al. |

FOREIGN PATENT DOCUMENTS

| | | | | |
|---|---|---|---|---|
| KR | 10-2047319 B1 | 11/2019 | | |
| WO | WO-2004096326 A1 | * 11/2004 | ............ | A61J 1/2096 |
| WO | 2012/023955 A1 | 2/2012 | | |
| WO | 2014145959 A1 | 9/2014 | | |
| WO | 2017/091643 A1 | 6/2017 | | |

OTHER PUBLICATIONS

In re James T. Doubet, et al., U.S. Appl. No. 16/895,370, filed Jun. 8, 2020, Office Action, dated Oct. 15, 2020, 25 pages.
PCT Application PCT/US2020/048978, International Search Report dated Nov. 10, 2020 (2 pages).
PCT Application PCT/US2020/048978, Written Opinion of the International Searching Authority dated Nov. 10, 2020 (6 pages).
PCT Application PCT/US2019/036774, International Search Report dated Sep. 16, 2019 (2 pages).
PCT Application PCT/US2019/036774, International Search Report and Written Opinion dated Sep. 16, 2019 (7 pages).
PCT Application PCT/US2020/061523, International Search Report dated Feb. 9, 2021 (3 pages).
PCT Application PCT/US2020/061523, Written Opinion of the International Searching Authority dated Feb. 9, 2021 (8 pages).
PCT Application PCT/US2019/056282, International Search Report dated Jan. 7, 2020 (2 pages).
PCT Application PCT/US2019/056282, Written Opinion of the International Searching Authority dated Jan. 7, 2020 (5 pages).
In re James T. Doubet, U.S. Appl. No. 16/393,696, filed Apr. 24, 2019, Office Action, dated Jan. 10, 2020, 16 pages.
In re James T. Doubet, et al., U.S. Appl. No. 16/563,896, filed Sep. 8, 2019, Office Action, dated Jan. 10, 2020, 11 pages.
In re James T. Doubet, et al., U.S. Appl. No. 16/698,471, filed Nov. 27, 2019, Office Action, dated Jan. 10, 2020, 14 pages.
"(Revised) List of Patents or Patent Applications to be Treated as Related". Feb. 26, 2020. 2 pages.
In re James T. Doubet, et al., U.S. Appl. No. 16/563,896, filed Sep. 8, 2019, Office Action, dated Jan. 14, 2021, 22 pages.
In re James T. Doubet, et al., U.S. Appl. No. 16/203,858, filed Nov. 29, 2018, Office Action, dated Jan. 21, 2021, 17 pages.
In re James T. Doubet, et al., U.S. Appl. No. 16/895,370, filed Jun. 8, 2020, Office Action, dated Feb. 8, 2021, 22 pages.
In re James T. Doubet, et al., U.S. Appl. No. 16/166,111, filed Oct. 21, 2018, Office Action, dated Jan. 11, 2021, 22 pages.
"(Revised) List of Patents and/or Patent Applications to be Treated as Related". Feb. 10, 2021. 2 pages.
PCT Application PCT/US2019/036774, International Preliminary Report on Patentability dated Dec. 15, 2020 (6 pages).
PCT Application PCT/US2019/062926, International Search Report dated Feb. 12, 2020 (2 pages).
PCT Application PCT/US2019/062926, Written Opinion of the International Searching Authority dated Feb. 12, 2020 (6 pages).
In re James T. Doubet, et al., U.S. Appl. No. 16/166,111, filed Oct. 21, 2018, Office Action, dated Apr. 3, 2020, 21 pages.
In re James T. Doubet, et al., U.S. Appl. No. 16/203,858, filed Oct. 21, 2018, Office Action, dated Apr. 3, 2020, 22 pages.
In re James T. Doubet, et al., U.S. Appl. No. 16/563,896, filed Sep. 8, 2019, Office Action, dated Aug. 27, 2020, 21 pages.
In re James T. Doubet, et al., U.S. Appl. No. 16/166,111, filed Oct. 21, 2018, Office Action, dated Sep. 4, 2020, 20 pages.
In re James T. Doubet, et al., U.S. Appl. No. 16/203,858, filed Nov. 29, 2018, Office Action, dated Sep. 22, 2020, 25 pages.
"(Revised) List of Patents and/or Patent Applications to be Treated as Related". Sep. 29, 2020. 2 pages.
In re James T. Doubet, U.S. Appl. No. 16/393,696, filed Apr. 24, 2019, Office Action, dated Jun. 27, 2019, 17 pages.
"List of Patents or Patent Applications to be Treated as Related". Aug. 4, 2019. 2 pages.
"(Revised) List of Patents or Patent Applications to be Treated as Related". Sep. 27, 2019. 2 pages.
Colomer, S., et al., "Syringeability and Viscosity Comparative of Different Florfenicol Formulations", publication date unknown, printed from http://marketing.hipra.com/SELECTNEWS/trials/Syringeabiliy_viscosity_comparative_of_FLORFENICOL_formulations.pdf on May 14, 2018. 1 page.

* cited by examiner

SYRINGE ADAPTER FOR ANIMAL MEDICATION

BACKGROUND

The present invention relates to an improved apparatus for use with animal medication, particularly for higher-viscosity medication.

Animals need medication for various purposes, including illness treatment and illness prevention.

BRIEF SUMMARY

The present invention is directed to an improved apparatus for use with animal medication. In one aspect, a syringe adapter for withdrawing fluid medication from a container comprises a sidewall extending between a proximal end and a distal end, the sidewall having an interior surface defining a chamber, the proximal end configured to be connected to a syringe while withdrawing at least a portion of the fluid medication from the container through the chamber and into a barrel of the syringe and the distal end configured for inserting into the container for the withdrawal, wherein an opening at the distal end is relatively large in diameter to facilitate withdrawing fluid medication having a relatively high viscosity and the syringe adapter is configured to be removed from the syringe and replaced with a needle prior to subsequently injecting, into an animal, the fluid medication withdrawn into the barrel. The relatively large opening is directed toward improved syringeability of the fluid medication. The viscosity of the fluid medication is preferably greater than or equal to 50 centipoise units when a temperature of the fluid medication is at least 5 degrees Celsius.

The syringe is preferably configured as a pistol-grip syringe or a tab-handled syringe, and therefore is directed toward improving leverage for the subsequent injection. Preferably, the diameter of the opening at the distal end is approximately 0.10 inches, and the sidewall is approximately 0.05 inches in thickness at the distal end. Optionally, the syringe adapter further comprises a flanged area that extends perpendicularly from the proximal end. The syringe adapter may further comprise a radial extension member that extends perpendicularly and radially outward from an exterior surface of the syringe adapter Preferably, an outer shape of the syringe adapter is generally conical in a first portion and generally cylindrical in a second portion. Preferably, an inner shape of the syringe adapter, for at least a portion of the proximal end, is generally conical. The inner shape of the syringe adapter may taper from the proximal end toward the distal end, for at least a portion of the proximal end, at approximately 6 percent. The syringe adapter preferably connects to the syringe using a Luer-type connection, the Luer-type connection selected from the group comprising a Luer-type lock and a Luer-type slip.

In another aspect, a method of administering fluid medication to an animal comprises: affixing a syringe adapter to a syringe, the syringe adapter comprising a sidewall extending between a proximal end and a distal end, the sidewall having an interior surface defining a chamber, the proximal end configured to be connected to a distal end of the syringe; inserting the distal end of the syringe adapter into a container of fluid medication having a relatively high viscosity; withdrawing, from the container, at least a portion of the fluid medication through the chamber and into a barrel of the syringe, wherein an opening at the distal end is relatively large in diameter to facilitate withdrawing the relatively-high-viscosity medication; removing the syringe adapter from the syringe subsequent to the withdrawing; affixing a needle to the distal end of the syringe, subsequent to the removing; and injecting, into an animal, the fluid medication withdrawn into the barrel.

Various embodiments of these and other aspects of the present invention may be provided in view of the present disclosure. It should be noted that the foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention, as defined by the appended claims, will become apparent in the non-limiting detailed description set forth below.

BRIEF DESCRIPTION OF THE SEVERAL VIEWS OF THE DRAWINGS

The present invention will be described with reference to the following drawings, in which like reference numbers denote the same element throughout.

DETAILED DESCRIPTION

As noted earlier, animals need medication for various purposes, including illness treatment and illness prevention. Treatment of animals using medication may be desired whether the animal is a family pet, part of a livestock operation, is the subject of research, and so forth. Examples of medicating animals for illness treatment will be obvious, and may span a wide variety of illnesses. One example of medicating an animal for illness prevention is a proactive vaccination; another example is to proactively administer an antibiotic. In a commercial livestock operation, animals may be proactively medicated before they are introduced into another group of livestock, for example to guard against introducing an illness that they may carry or simply to ensure that all animals in the group have received an identical medication regimen. Medication might also be administered in anticipation of, or in response to, a change in weather conditions or a change in geographical location for an animal (such as moving from one climate to another). Hereinafter, animal medications are discussed without differentiation of the purpose for such medication.

Animal medication may be found in various forms, including solid and fluid. Solid substances may be ingestible, for example, while fluids may be injectable or may be administered orally or nasally. Embodiments of the present invention are directed toward improved apparatus for use with animal medication in fluid form.

Medications provided in fluid form may vary widely in their viscosity, depending upon their chemical formulation. Viscosity is sometimes defined as the resistance of a substance to flow. The viscosity of water is relatively low, for example, while the viscosity of honey is relatively high. The viscosity of some substances can be changed by applying heat; for example, melting butter increases its ability to flow. Some fluid medications may have a viscosity that is relatively low and is similar to that of water, for example, and thus will flow quite easily. Other medications are known that have a viscosity that is markedly different from water.

Fluid medications intended for use with animals are commonly marketed in multi-dose packaging, such as bottles that hold enough fluid for administering several doses. A bottle of medication might hold 500 milliliters, for example (equivalently, 500 cubic centimeters), which is roughly equivalent to 16.9 ounces. The bottle might be made of glass or plastic, and a container having a configuration other than a bottle might be used. Hereinafter, the term "bottle" is used for ease of reference, and by way of illustration and not of limitation, as a container type in which medication may be contained.

One reason for marketing animal medication in multi-dose bottles is economic. The cost of the medication may be reduced, for example, by selling a larger quantity container and thereby reducing the relative cost of the packaging. Another reason for marketing animal medication in multi-dose bottles is that the dosage of many (if not all) medications is prescribed with regard to the animal's body weight. Accordingly, the correct amount of medication to use on a particular animal can be calculated and then withdrawn from the multi-dose bottle, after which it may be injected into the animal, and the remaining medication is then available for subsequent use.

Figure 1:
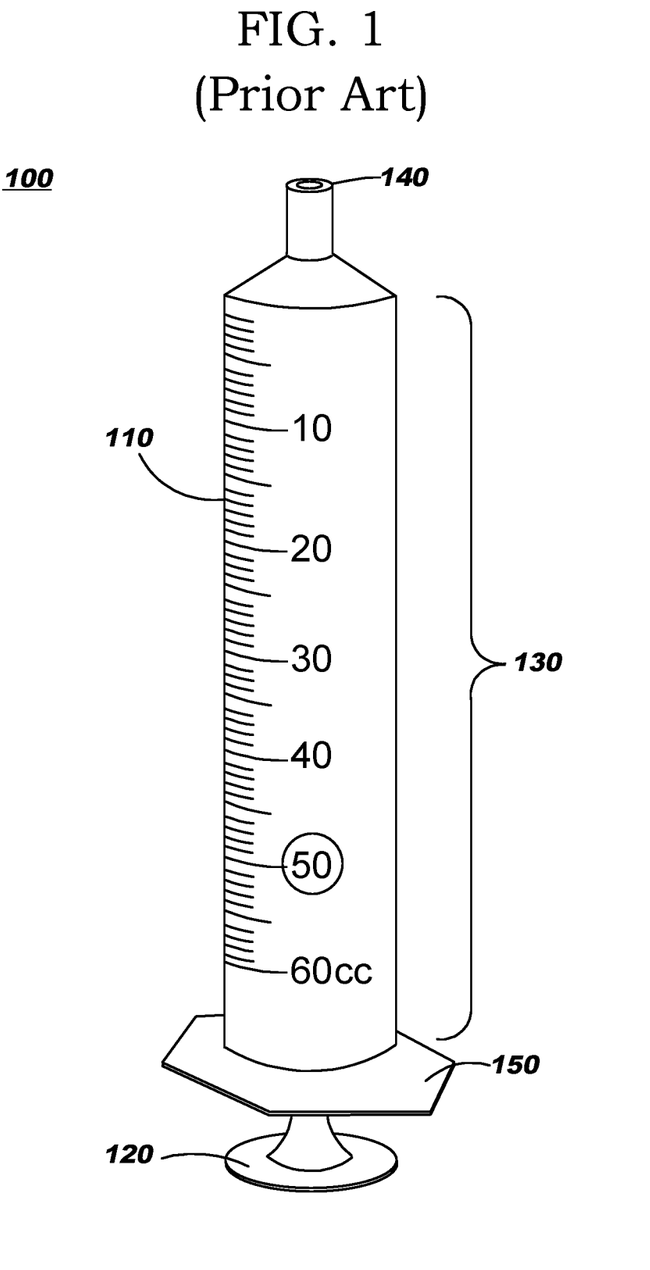
FIGS. 1-3 depict examples of prior art syringes.

A multi-dose bottle of fluid medication is typically marketed with a rubber membrane covering at least a portion of an opening at the top of the bottle. Conventionally, the fluid medication is withdrawn from such bottle by placing a needle onto the tip of a syringe, inserting a tip of the needle into the rubber membrane, and withdrawing a plunger of the syringe until an appropriate amount of fluid is pulled into the syringe body (referred to herein as the syringe "barrel"); this same needle is then used for injecting the medication from the syringe into the animal. FIG. 1 shows an example of a prior art syringe 100, and illustrates how the hollow barrel 130 of syringe 100 is commonly marked with fill lines 110 that are provided for measuring the amount of fluid contained therein. A needle is placed over the tip 140, and fluid enters through an opening or eye of the needle and into the syringe barrel 130. The syringe includes a retractable plunger, a terminal end of which is shown at 120. (As will be obvious, as fluid medication is withdrawn from the bottle into the barrel 130, the plunger 120 movably extends outward from the proximal end of the syringe 100, although this is not illustrated in FIG. 1.) Commonly, a syringe as illustrated in FIG. 1 is constructed of plastic, making it relatively cheap to purchase.

A tab-shaped member 150 is also provided on syringe 100. When administering the medication from the barrel 130, a person's index finger is placed on the tab-shaped member 150 at one side of barrel 130 and the person's middle finger is placed on the tab-shaped member 150 at the opposing side of barrel 130, and the person's thumb is then used to depress the terminal end of plunger 120 into the barrel in order to expel the medication from the barrel.

Figure 2:
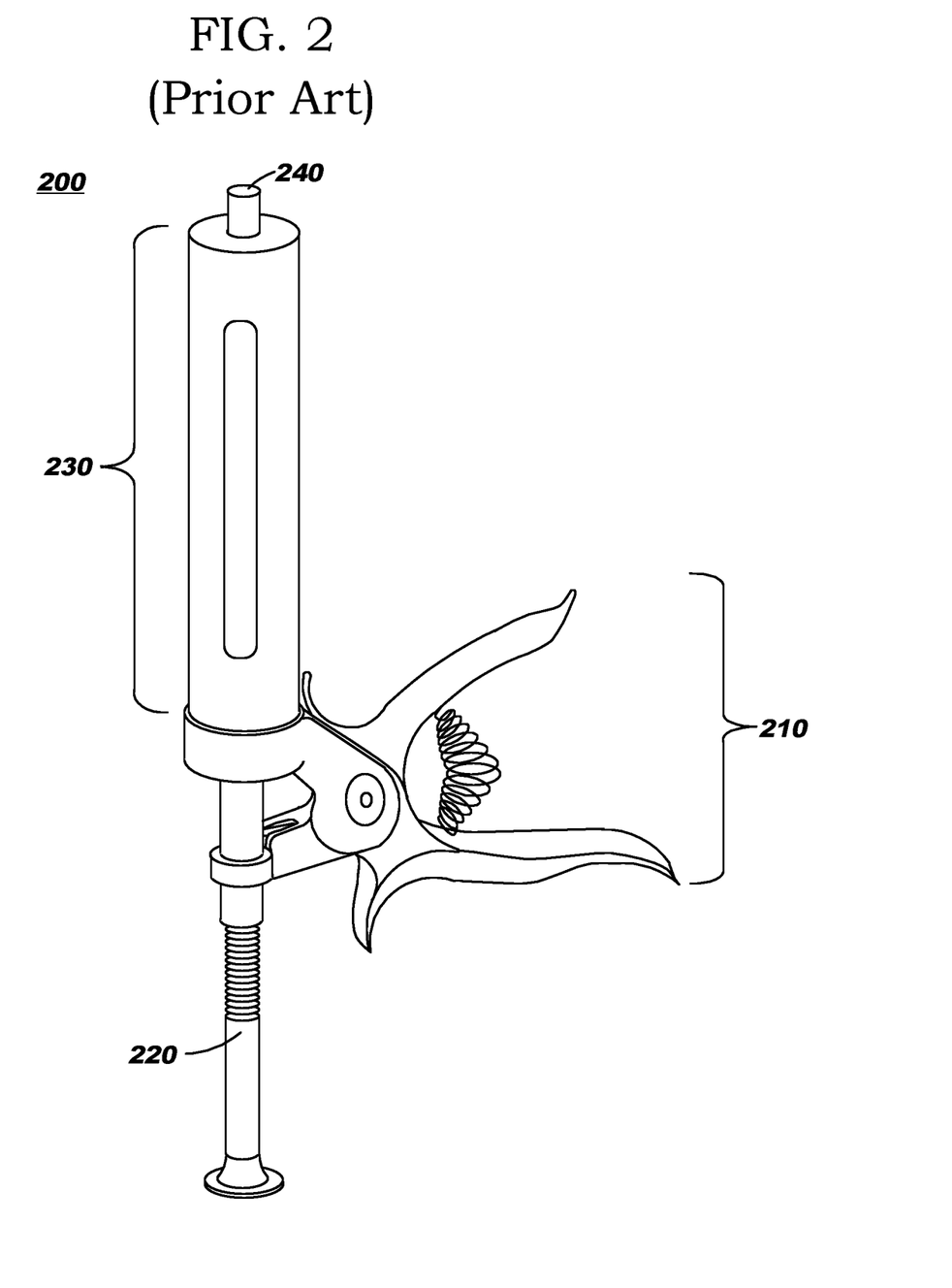

As an alternative to the syringe 100 of FIG. 1, an example of a so-called "pistol-grip" syringe is illustrated in FIG. 2. Fluid medication is drawn into a syringe of this type by pulling plunger 220 outwardly from the barrel 230. A tab-shaped member is not provided on a syringe of this type, as compressing or squeezing the handles 210 serves to expel medication from the barrel of a syringe having a pistol-grip configuration.

Figure 3:
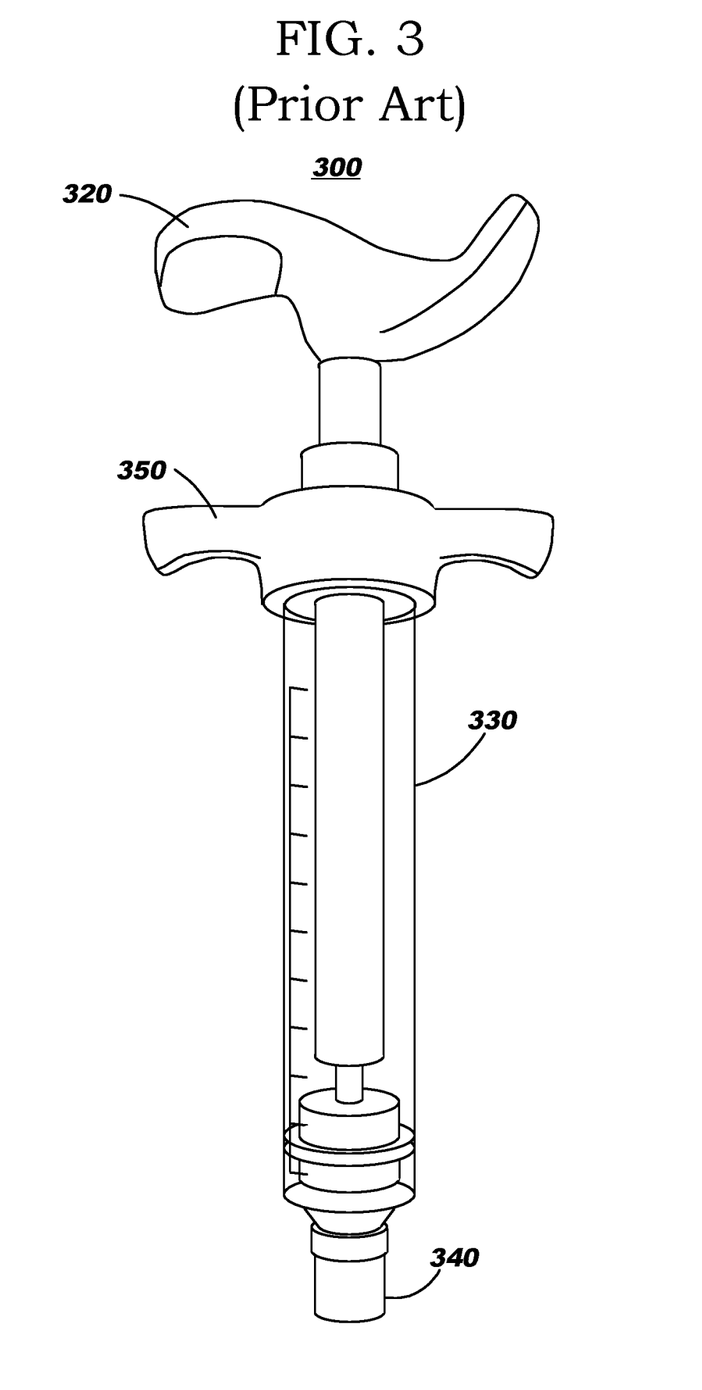

FIG. 3 illustrates yet another prior art syringe 300, and is referred to herein as a "tab-handled" syringe. In this configuration, the syringe has a tabbed member 350 near the proximal end of barrel 330, and includes a handle-style tabbed member 320 affixed to the terminal end of the plunger. The tabbed member 350 is used in a similar manner to tab-shaped member 150 of FIG. 1, whereby a person places fingers on the tabbed member 350 on opposing sides of barrel 330; the person then presses down on tabbed member 320 using the person's palm to depress the terminal end of the plunger into the barrel in order to expel the medication from the barrel. As compared to tab-shaped member 150 and plunger end 120 of FIG. 1, the tabbed members 320, 350 of FIG. 3 typically provide improved comfort for the person using the tab-handled syringe.

The tips 240, 340 may be generally on the order of ⅜ to 7/16 inch in diameter and generally of similar height (and similarly, tip 140), and are generally constructed of metal. An interior area of this tip is intended for securably attaching a needle and is generally threaded for at least a portion thereof. A height of this threaded area is generally on the order of ⅛ inch. (Notably, tips 240, 340 are not designed for inserting through the rubber membrane of a medicine bottle.)

Figure 4:
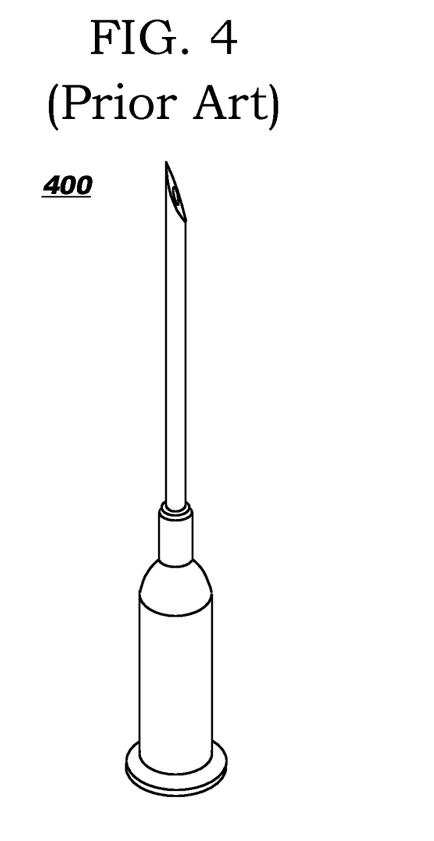
FIG. 4 depicts an example of a prior art needle.
Figure 4A:
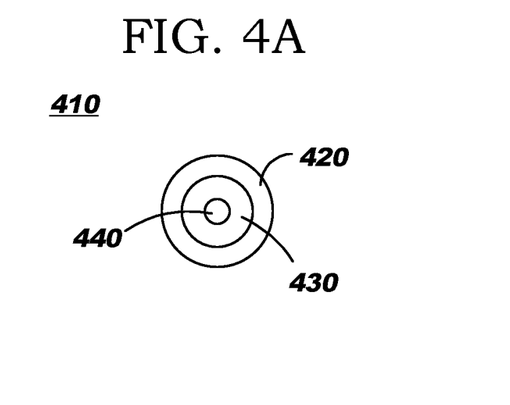
FIGS. 4A and 4B illustrate bottom views showing how a proximal end of a needle may be configured for securable attachment to a syringe.
Figure 4B:
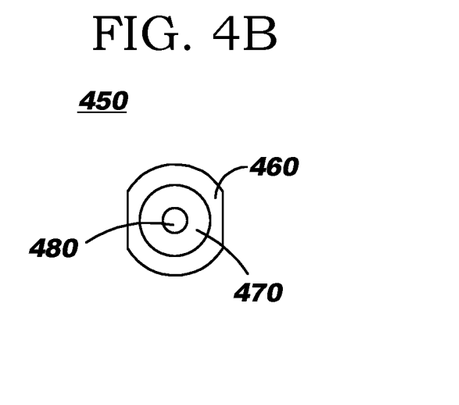

FIG. 4 illustrates an example of a prior art needle 400, which may be affixed to the distal end of syringes 100, 200, or 300. Needles are typically sold in standardized sizes, and thus the distal syringe ends 140, 240, 340 typically conform to the standard size of the proximal end of a needle. FIGS. 4A and 4B illustrate bottom views showing examples of how a proximal end of needle 400 may be configured for securable attachment to the distal end of a syringe that has an internal threaded portion. In an approach 410 as shown in FIG. 4A, a flanged area 420 extends perpendicularly and radially outward from the proximal end of the needle (as is generally illustrated in FIG. 4). Reference number 440 depicts the opening in the tip of the needle, and reference number 430 generally depicts the interior surface of sidewalls of needle 400. In another approach 450 as shown in FIG. 4B, a flanged area 460 extends perpendicularly outward from the proximal end of the needle, but in this configuration, is fashioned as having side edges that are not generally round. Reference number 480 depicts the opening in the tip of the needle, and reference number 470 generally depicts the interior surface of sidewalls of needle 400. In either case, a flanged area 420, 460 on the proximal end of a needle is designed to securably attach to a corresponding receiving area on the distal end of a syringe. In yet another approach (not illustrated), the securable attachment of a needle to a syringe tip relies on friction instead of an exterior flanged area, whereby the proximal end of needle 400 is placed over an exterior of the distal end (e.g., tip 140 of FIG. 1) of a syringe. These approaches are commonly referred to as a Luer-style lock approach and a Luer-style slip approach, respectively, as is discussed in further detail below.

For withdrawing fluid medication from a bottle into the barrel of syringe 100, 200, or 300 using known techniques, the sharp tip at the distal end of the needle 400 is inserted through the rubber membrane of the bottle. For subsequently administering the fluid medication from the barrel of the syringe, the sharp tip of that same needle is inserted into an animal's body, and the person holds tab-shaped member 150 while simultaneously depressing plunger 120 of syringe 100, squeezes the handles 210 of pistol-grip syringe 200, or holds tabbed member 350 while simultaneously depressing handle-style tabbed member 320 of tab-handled syringe 300.

This known approach of withdrawing fluid medication from a bottle using a needle and then administering the medication using the same needle works well for fluids having a low viscosity. (Consider, by way of reference, the relative ease of drawing a low-viscosity fluid such as water through the tip/opening of a needle 400 affixed to a syringe.) However, animal medications are marketed that have a relatively high viscosity (that is, they are relatively thick in consistency), and this higher viscosity makes the medications very difficult to withdraw from a bottle using a needle, and also typically more difficult to expel from the syringe. Stated another way, such higher-viscosity medications are not readily "syringeable".

When a medication is not readily syringeable, it may take a considerable amount of time for the person tasked with withdrawing the medication from the bottle to withdraw even a small amount of medication. When a large amount of such medication must be administered, and/or when the higher-viscosity medication must be administered to multiple animals, the person may experience frustration or even fatigue due to this long withdrawal time. As a result, use of the higher-viscosity medication by animal care-givers may be diminished, which may lead to the medication failing to reach its potential market share. Thinning the medication is undesirable as an answer to improving the syringeability problem, as the effectiveness of the medication could be altered.

In addition to the above-described issues with withdrawing higher-viscosity medication into a syringe, the higher viscosity of the medication makes the injection process more time-consuming and physically more difficult for the person tasked with medicating the animal. In particular, the general configuration of a plastic syringe as illustrated in FIG. 1 does not enable a person using the syringe to have sufficient leverage when attempting to inject the medication into an animal. Tab-shaped member 150 is known to collapse or break in some instances, due to the physical force that must be exerted while depressing plunger 120. The plunger shaft is also known to break in some instances, for example due to misalignment as it moves within the barrel or due to age-related brittleness. These problems are more likely to occur with the increased physical force required for injecting higher-viscosity medications.

In sharp contrast to use of a plastic syringe, the syringes 200, 300 of FIGS. 2-3 are better adapted for withstanding the physical force required for expelling a higher-viscosity medication from the syringe barrel and for allowing the person using the syringe to have better leverage during the injection process. (Because the leverage is improved, the time required to complete the injection may be shortened as compared to use of a plastic syringe configured as shown at 100 of FIG. 1, which benefits the person and the animal.)

In view of the above-described issues, preferred embodiments of the present invention are directed toward improved syringeability of medications having a relatively high viscosity. (The disclosed syringe adapter may function suitably with lower-viscosity medications as well, and is therefore not deemed to be limited to use with particular medications.)

A preferred embodiment of the present invention provides a new tip that operates as a syringe adapter for withdrawing medication from a bottle. This tip is preferably affixed to a pistol-grip syringe of the type illustrated in FIG. 2 or a tab-handled syringe of the type illustrated in FIG. 3. The pistol-grip or tab-handled syringe may be formed from plastic, metal, or other substance(s). Accordingly, use of an embodiment of the present invention addresses the issue of drawing a higher-viscosity fluid from a bottle as well as the issue of providing sufficient leverage for subsequent injection. That is, the larger opening of the disclosed syringe adapter addresses syringeability issues by improving draw time of higher-viscosity medications and, because this adapter is affixed to a pistol-grip or tab-handled syringe, the medication withdrawn into the pistol-grip or tab-handled syringe can be more easily administered from the syringe barrel (noting that the syringe adapter will be replaced with a needle prior to injecting the medication).

Figure 5:
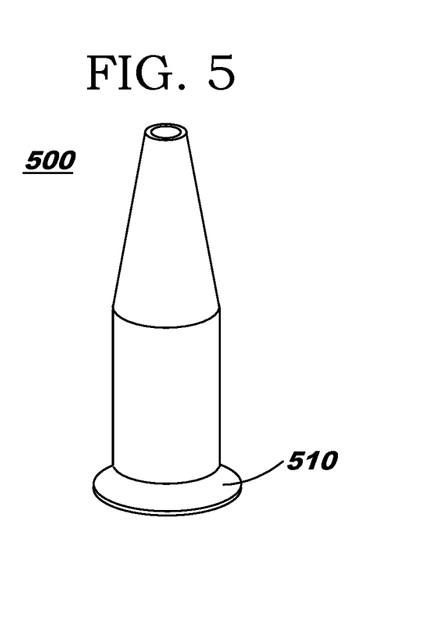
FIGS. 5-6 illustrate first and second preferred embodiments of the syringe adapter disclosed herein.

FIG. 5 illustrates one embodiment of the syringe adapter disclosed herein. The syringe adapter has a sidewall extending between a proximal end and a distal end, and the interior surface of the sidewall defines a chamber through which fluid medication flows. The length and shape of the syringe adapter, as well as the thickness of portions of the sidewall and the width of its interior chamber, may vary without deviating from the scope of the present invention. In the embodiment illustrated in FIG. 5, the shape of the syringe adapter 500 is generally conical in an upper portion and generally cylindrical in a lower portion. While not illustrated in FIG. 5, an interior of at least a portion of the lower portion is preferably tapered, with a 6 percent taper extending from the proximal end toward the distal end. This tapered shape conforms the interior surface to International Standard ISO 594-2:1998(E) and its replacement ISO 80369-7:2016, which are directed toward conical fittings for health-care applications. Preferably, the overall length of the syringe adapter is not shorter than ⅜ to ½ inch, by way of illustration but not of limitation, as this length will enable the syringe adapter to sufficiently extend into a bottle of medication to be withdrawn. An upper range of the overall length, conversely, may be on the order of 1 to 2 inches.

A preferred diameter of the hole in the distal end of the tip of the syringe adapter is on the order of 0.10 inches, although embodiments are not limited to this diameter. Thickness of the sidewall of the syringe adapter is preferably on the order of 0.050 inches, although embodiments are not limited to this thickness. Using a sidewall thickness of 0.050 inches and an opening of 0.10 inches results in a syringe adapter having an overall diameter of 0.20 inches at the end to be inserted into the bottle of medication, in this example configuration.

Preferably, the proximal end of the disclosed syringe adapter attaches to a syringe using a Luer-type lock or a Luer-type slip. Luer-type locks and Luer-type slips are known approaches for making leak-free connections on fluid fittings, and are described in the above-cited International Standards. A Luer-type lock provides a threaded attachment, whereby two pieces of a configuration are held together by rotating a flanged area (such as flanged area 420 of FIG. 4A or 460 of FIG. 4B) of one piece within threads of the other piece, whereas a Luer-type slip is non-threaded and provides attachment using friction. In one approach for securably attaching syringe adapter 500 using a Luer-type lock, the syringe adapter 500 as illustrated in FIG. 5 has an external flanged area 510 on the proximal end, and a two-part connection is made by inserting this flanged end into corresponding internal threads on a distal end of a syringe (as illustrated at 240, 340). As noted earlier, a conventional height for this internal threaded portion of a pistol-grip syringe is approximately ⅛ inch in length, and accordingly, a flanged area 510 on the proximal end of syringe adapter 500 is preferably on the order of 1/16 to ⅛ inch in height. The shape of flanged area 510 may correspond generally to flanged area 420 or 460 (for example, by extending perpendicularly and radially from the proximal end of the syringe adapter, although a strictly circular shape is not required), although another shape providing for a securable attachment may be used without deviating from the scope of the present invention.

In another approach, the proximal end of the syringe adapter 500 may omit the flanged area shown at 510 and is attached and held to the distal end of the syringe by friction in a Luer-type slip approach.

Figure 6:
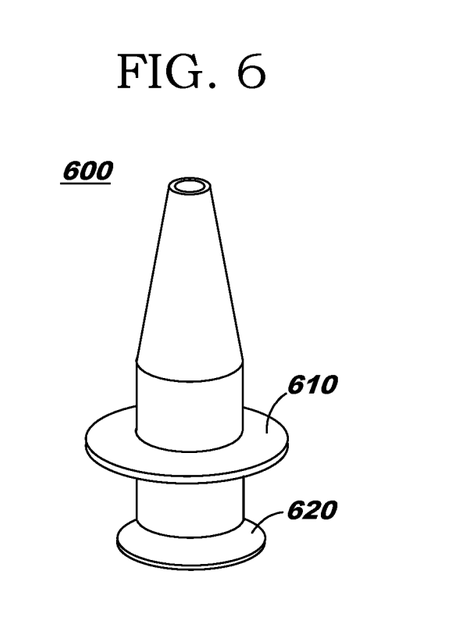

FIG. 6 illustrates another embodiment of the syringe adapter disclosed herein. In this embodiment, syringe adapter 600 includes a radial extension feature 610, which is preferably configured as extending perpendicularly and radially outward from the body of the syringe adapter and is shown in FIG. 6 as being located relatively near to the proximal end of syringe adapter 600. (Alternatively, radial extension feature 610 may be placed at another location on the syringe adapter, for example being located closer to the conical portion thereof.) In addition to enabling a person to more easily grasp the syringe adapter 600, the radial extension feature 610 also serves to prevent inserting the syringe into the medication bottle far enough that the attachment point (e.g., Luer-type slip or lock) between the syringe and the syringe adapter would come into contact with the medication. Accordingly, in a preferred embodiment, a diameter of radial extension feature 610 is sufficiently large as to exceed the diameter of a conventional rubber membrane on a medicine bottle. The diameter of radial extension feature 610 may be, by way of example, on the order of twice the diameter of the cylindrical portion of syringe adapter 600. (Syringe adapter 600 may omit the flanged area 620 when relying on a Luer-type slip attachment, as was discussed above with reference to flanged area 510.)

A preferred material for the disclosed syringe adapter is plastic, which will allow it to be economically produced as a disposable item, although another material may be used without deviating from the scope of the present invention. Notably, the disclosed syringe adapter does not need to come into physical contact with a particular animal (i.e., because the syringe adapter will be replaced with a needle in order to inject the medication), and thus re-use of the syringe adapter for medicating multiple animals need not introduce cross-contamination concerns.

Use of the disclosed syringe adapter while medicating an animal operates as follows: the syringe adapter is affixed to a syringe (which, as noted earlier, is preferably a pistol-grip or tab-handled syringe); the syringe adapter is inserted into a bottle of medication; the plunger of the syringe is pulled back to withdraw the desired dosage of medication from the bottle into the syringe barrel; the syringe adapter is removed from the bottle, while the plunger remains stationary; the syringe adapter is replaced with a needle; and the medication is then injected into an animal by squeezing the pistol-grip handles or pressing down on the tabbed handle and thereby pushing the plunger forward to empty the syringe barrel. If it is desired to reuse the syringe adapter, then the needle is removed from the syringe, after which the above process is repeated.

Figure 7:
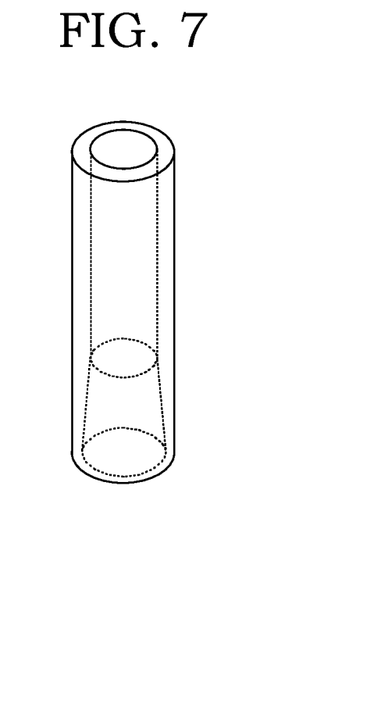
FIGS. 7-8 illustrate alternative embodiments of the syringe adapter disclosed herein.
Figure 8:
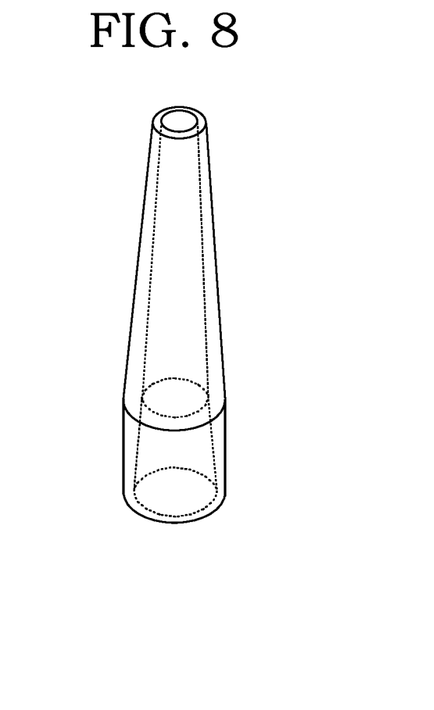

While FIGS. 5 and 6 illustrate a syringe adapter shape that is generally conical in an upper portion and generally cylindrical in a lower portion, this is by way of illustration and not of limitation. As one alternative embodiment, an outer shape of the syringe adapter may be generally cylindrical while preferably having a tapered interior shape for at least a portion of the proximal end, noting that such interior taper enables the syringe adapter to comply with the above-cited International Standards. This alternative embodiment is illustrated in FIG. 7, where dashed lines are used to illustrate a general shape of the interior. FIG. 8 provides another alternative embodiment, where an outer shape of the syringe adapter may be generally conical in an upper portion and generally cylindrical in a lower portion, and in this alternative, the relative length of the upper and lower portions varies from the embodiment illustrated in FIGS. 5 and 6 (and again, at least a portion of such configuration preferably has a tapered interior shape at the proximal end, as shown by the dashed lines, to thereby conform to the above-cited International Standards). Notably, as compared to the cylindrical exterior shape as illustrated in FIG. 7, the exterior taper of the upper portion as illustrated in FIGS. 5-6 and 8 may tend to provide a better seal, and thus be less likely to leak, during such time as the syringe adapter is inserted through the rubber membrane of a bottle. While not illustrated in FIG. 7 or 8, a radial extension member (such as that shown at reference number 610 of FIG. 6) may be added to these configurations if desired.

It should be noted that while preferred embodiments are described herein as conforming to the above-cited International Standards and/or as using Luer-type connections to a syringe, this is by way of illustration but not of limitation. It should also be noted that the figures are directed toward illustrating aspects of the present invention, in combination with descriptions herein, and aspects shown therein (for example, length, width, and/or taper) are not necessarily drawn to scale.

While medications have been discussed herein as commonly being sold in a multi-dose bottle, this is by way of illustration and not of limitation. The disclosed syringe adapter may be used beneficially for medication that is sold in a single-use dosage.

Advantageously, the disclosed syringe adapter may be included with purchase (e.g., within the packaging) of a higher-viscosity medication. As one alternative, a multi-pack of the disclosed syringe adapter may be included with such purchase, particularly when the medication is sold in a multi-dose bottle. The disclosed syringe adapter may also be sold separately from medication.

Examples of higher-viscosity animal medications with which the disclosed syringe adapter may be used beneficially include Nuflor® and Resflor Gold®. ("Nuflor" and "Resflor Gold" are registered trademarks of Intervet Inc. in the United States, other countries, or both. Intervet is now known as "Merck Animal Health".) These medications are commonly sold in 500-milliliter multi-dose bottles and may be administered, by way of example, in dosages of 36 to 60 milliliters per animal. Accordingly, a single multi-dose bottle may be used to treat generally 8 to 14 animals at this dosage range.

As noted earlier, viscosity of a substance may vary with temperature. Viscosity is commonly measured in units termed "centipoise", which may be abbreviated as "cP" or "cps". Water, at 70 degrees Fahrenheit, has a viscosity of approximately 1 cps, and by way of comparison, blood generally has a viscosity of about 10 cps. According to a study documented in "Syringeability and Viscosity Comparative of Different Florfenicol Formulations" by S. Colomer, et al., date unknown, the viscosity of Nuflor® at 5 degrees Celsius (which is approximately 41 degrees Fahrenheit) was 321 cps.

An embodiment of the present invention is believed to be advantageous for fluid medications having a viscosity of at least 50 to 100 cps at a temperature of at least 5 degrees Celsius, as well as for fluid medications having a higher cps at this temperature (noting, as stated above, that viscosity varies with temperature).

As has been demonstrated, an embodiment of the present invention improves syringeability of higher-viscosity medications, allowing such medication to be withdrawn from a bottle in much less time as compared to the known approach of withdrawal using a needle. More animals may therefore be medicated in a given period of time, leading to improved productivity of persons caring for the animals as well as enabling overall improved health for the animals. No longer will higher viscosity be a barrier to the market, and because medication of this type will be more readily administered when using a syringe adapter as disclosed herein, improvement may be expected in animal health, and market share and/or market presence for the medication may improve as well.

It should be noted that various features discussed herein with reference to "an embodiment", "one embodiment", "a preferred embodiment", and so forth should not be construed as suggesting that each such feature is present in a single embodiment, or in every embodiment, of the present invention. Instead, it should be understood that there may be various combinations of the disclosed features present in any particular embodiment.

While embodiments of the present invention have been described, additional variations and modifications in those embodiments may occur to those skilled in the art once they learn of the basic inventive concepts. Therefore, it is intended that the appended claims shall be construed to include the described embodiments and all such variations and modifications as fall within the spirit and scope of the invention.

The invention claimed is:

1. A syringe adapter connectable to a syringe tip of a syringe for withdrawing fluid medication from a container into a barrel of the syringe and comprising:
    a sidewall extending between a proximal end and a distal end opposite the proximal end, the sidewall having an interior surface defining a chamber, the distal end of the sidewall being a distal end of the syringe adapter, the distal end of the syringe adapter being frustoconical in exterior shape such that the interior surface of the distal end of the sidewall defines a distal end of the chamber as being frustoconical, a terminal edge of the distal end of the sidewall defining a first opening into the chamber and a terminal edge of the proximal end of the sidewall defining a second opening into the chamber, the proximal end of the sidewall connectable to the syringe tip for withdrawing at least a portion of the fluid medication from the container through the first opening and into the chamber and then into the barrel of the syringe and the distal end of the sidewall configured for inserting into the container for the withdrawal, wherein:
    the first opening is approximately 0.10 inches in inner diameter to facilitate withdrawing, from the container, fluid medication having a relatively high viscosity;
    upon connecting the proximal end of the sidewall to the syringe tip, the second opening aligns with an opening into the barrel of the syringe, the opening into the barrel located in the syringe tip of the syringe, thereby providing a fluid path between the first opening and the barrel, the fluid path passing through the chamber; and
    the syringe adapter is disconnectable from the syringe tip of the syringe to enable replacement thereof on the syringe tip with a needle after withdrawing the withdrawn portion of the fluid medication and prior to subsequently injecting, into an animal with the needle, the withdrawn portion of the fluid medication.

2. The syringe adapter according to claim 1, wherein the inner diameter of the first opening improves syringeability of the fluid medication.

3. The syringe adapter according to claim 1, wherein the relatively high viscosity of the fluid medication is at least approximately 50 centipoise units when a temperature of the fluid medication is approximately 5 degrees Celsius.

4. The syringe adapter according to claim 1, wherein the relatively high viscosity of the fluid medication is greater than or equal to 50 centipoise units when a temperature of the fluid medication is at least 5 degrees Celsius.

5. The syringe adapter according to claim 1, wherein the syringe is configured as a pistol-grip syringe to thereby improve leverage for the subsequent injection with the needle.

6. The syringe adapter according to claim 1, wherein the syringe is configured as a tab-handled syringe.

7. The syringe adapter according to claim 1, wherein the proximal end of the sidewall of the syringe adapter connects to the syringe tip of the syringe using a Luer-type connection, the Luer-type connection selected from the group consisting of a Luer-type lock and a Luer-type slip.

8. The syringe adapter according to claim 1, wherein the sidewall is approximately 0.05 inches in thickness at the distal end.

9. The syringe adapter according to claim 1, further comprising a flanged area that extends perpendicularly from the proximal end of the sidewall, the flanged area enabling the connection to the syringe tip of the syringe.

10. The syringe adapter according to claim 1, further comprising a radial extension member that extends perpendicularly and radially outward from an exterior surface of the syringe adapter.

11. The syringe adapter according to claim 1, wherein an outer shape of the syringe adapter is generally conical in a first portion terminating at the first opening and generally cylindrical in a second portion.

12. The syringe adapter according to claim 1, wherein an outer shape of the syringe adapter tapers, for at least a portion thereof, from the proximal end toward the distal end.

13. The syringe adapter according to claim 1, wherein an inner shape of the syringe adapter, for at least a portion of the proximal end, is generally conical.

14. The syringe adapter according to claim 1, wherein an inner shape of the syringe adapter tapers from the second opening at the proximal end toward the distal end, for at least a portion of a length of the proximal end, at approximately 6 percent.

15. A syringe adapter configured to threadably attach to a syringe tip of a syringe for withdrawing fluid medication from a container into the syringe, comprising:
    a sidewall extending between a proximal end and a distal end located opposite the proximal end, the sidewall having an interior surface defining a chamber, wherein:
    the distal end of the sidewall is a distal end of the syringe adapter;
    the distal end of the syringe adapter is frustoconical in exterior shape;
    the interior surface of the distal end of the sidewall defines a distal end of the chamber as being frustoconical;
    a terminal end of the distal end of the sidewall defines a first opening into the chamber;
    the first opening is approximately 0.10 inches in diameter;
    a terminal end of the proximal end of the sidewall defines a second opening into the chamber; and the proximal end is configured with a flanged area that extends outwardly therefrom, the flanged area configured to provide a Luer-type locking connection for threadably attaching the syringe adapter to the syringe tip, the syringe tip located at a distal end of the syringe, wherein:

the syringe adapter is configured to remain threadably attached to the syringe tip while withdrawing fluid medication from the container through the first opening and into the chamber, the syringe adapter further configured for the withdrawn fluid medication to exit through the second opening and to enter into a barrel of the syringe through an opening in the syringe tip; and the syringe adapter is configured to be threadably removed from the syringe tip of the syringe after a desired amount of the fluid medication is withdrawn through the syringe adapter and into the barrel of the syringe.

16. The syringe adapter according to claim 15, wherein the syringe adapter is not configured to enable injecting the withdrawn medication into an animal.

17. A syringe adapter for flowing viscous fluid medication from a container to a syringe, the syringe adapter comprising:

a sidewall, the sidewall having a proximal end, an opposite distal end, and an interior surface defining an interior chamber extending from the proximal end to the opposite distal end, the distal end of the sidewall being a distal end of the syringe adapter, the distal end of the syringe adapter being frustoconical in exterior shape such that the interior surface of the distal end of the sidewall defines a distal end of the interior chamber as being frustoconical, a terminal edge of the distal end of the sidewall defining a first opening into the interior chamber and a terminal edge of the proximal end of the sidewall defining a second opening into the interior chamber;

a viscous fluid flow path extending through the interior chamber, between the first opening and the second opening, the first opening having an inner diameter of approximately 0.10 inches; and a flanged area extending outwardly from the terminal edge of the proximal end for threadably engaging a threaded interior portion of a syringe tip formed as a needle-attachment point on a distal end of the syringe, wherein the first opening having the inner diameter of approximately 0.10 inches facilitates withdrawing the viscous fluid medication through the first opening into the interior chamber from the container and then flowing the viscous fluid medication via the viscous fluid flow path through the interior chamber and out the second opening, through an opening in the syringe tip, into a barrel of the syringe.

18. The syringe adapter according to claim 17, wherein a length of the syringe adapter, from the distal end to the proximal end, is between ⅜ inch and 2 inches.

19. The syringe adapter according to claim 17, wherein a viscosity of the viscous fluid medication is greater than or equal to 50 centipoise units when a temperature of the viscous fluid medication is at least 5 degrees Celsius.

20. The syringe adapter according to claim 17, wherein a shape of the interior chamber tapers from the proximal end of the sidewall toward the distal end of the sidewall, for at least a portion of a length of the proximal end of the sidewall, at approximately 6 percent.

* * * * *